(12) United States Patent
Bernstein

(10) Patent No.: US 6,740,330 B1
(45) Date of Patent: May 25, 2004

(54) METHOD OF TREATING ACNE VULGARIS AND COMPOSITION

(75) Inventor: Joel E. Bernstein, Deerfield, IL (US)

(73) Assignee: Sirius Laboratories, Inc., Vernon Hills, IL (US)

( * ) Notice: Subject to any disclaimer, the term of this patent is extended or adjusted under 35 U.S.C. 154(b) by 0 days.

(21) Appl. No.: 09/847,151

(22) Filed: May 2, 2001

(51) Int. Cl.[7] .............................. A61K 6/00; A61K 7/00; A01N 25/34
(52) U.S. Cl. ........................ 424/402; 424/401
(58) Field of Search ................. 424/402, 401

(56) References Cited

U.S. PATENT DOCUMENTS 4,749,080 A * 6/1988 Toohey ...................... 206/210
5,116,670 A * 5/1992 Suzuki et al. ............... 428/285

FOREIGN PATENT DOCUMENTS

JP 04275316 A * 9/1992
WO WO009320796 A1 * 10/1993

* cited by examiner

Primary Examiner—Thurman K. Page
Assistant Examiner—S. Howard
(74) Attorney, Agent, or Firm—Jones Day

(57) ABSTRACT

An article for use in the treatment of acne vulgaris comprises a cloth pledgette impregnated with a composition comprising benzoyl peroxide and an amount of acetone sufficient to solubilize the benzoyl peroxide. In a preferred embodiment, the article is packaged in an individual pouch. A method of manufacturing the article is disclosed.

28 Claims, No Drawings

METHOD OF TREATING ACNE VULGARIS AND COMPOSITION

BACKGROUND OF THE INVENTION

Acne vulgaris is an inflammatory disease of the sebaceous glands characterized by an eruption of the skin, often pustular in nature but not suppurative. Acne is a common affliction of the adolescent and affects a small but significant percentage of the adult population. Acne involvement results in unsightly lesions, particularly on the face, and in some cases results in severe scarring.

There are a variety of methods for treating acne vulgaris including administering various agents either orally or topically to the skin. Nevertheless, acne vulgaris is seldom cured and only can be controlled with difficulty.

One of the most common agents utilized to topically treat acne is benzoyl peroxide. Benzoyl peroxide is contained in a variety of over-the-counter and prescription acne products which take the form of lotions, creams or gels. The exact mode of action of benzoyl peroxide is unknown, but the best evidence suggests an antibacterial effect against an organism Propionibacterium acnes.

Tubes and bottles of acne medicines are the most common ways of packing such topical agents. However, tubes and bottles are inconvenient for patients to carry with themselves to school, camp, office, etc. Consequently, over the last decade a new method of delivering anti-acne agents has evolved based on incorporating active anti-acne ingredients into small cloth towelettes called pledgettes. These pledgettes can then be packaged in a sealed pouch that can be conveniently opened at the time of use. Additionally, since only one dose is opened at a time, several patients can "share" a box of such pledgettes without exposure to one another's germs, dirt, etc. Topical antibiotics are another popular prescription treatment for acne. Today, pledgettes containing topical antibiotics such as clindamycin and erythromycin are widely used for both their convenience, as well as their safety and efficacy.

While benzoyl peroxide would also be an ideal agent to incorporate into pledgettes for the treatment of acne, numerous attempts to incorporate benzoyl peroxide into pledgettes have been unsuccessful until the current invention. Since the benzoyl peroxide was not completely soluble in any of the vehicles tried, a considerable amount of the benzoyl peroxide was selectively "trapped" in the pledgette fibers, rendering the delivery of benzoyl peroxide to the skin uncertain. The applicant of this patent application had himself trial to produce benzoyl peroxide pledgettes several times in the 1980's and early 1990's without success for the very reason given above. However, surprisingly, the applicant has recently discovered a way or producing pledgettes such that the benzoyl peroxide is not selectively trapped in the pledgette material. I have found that by solubilizing benzoyl peroxide in vehicles containing moderate to high concentrations of acetone (from about 30% to 100%), pledgettes containing benzoyl peroxide in acetone compositions can be prepared such that the benzoyl peroxide is not selectively trapped in the pledgette. Consequently, the pledgette delivers the concentration of benzoyl peroxide contained in the acetone composition.

DETAILED DESCRIPTION OF THE INVENTION

In the following detailed description of the invention and in the claims, all percentage amounts are stated in terms of weight percent (% w/w).

In accordance with this invention, compositions are provided whereby benzoyl peroxide is incorporated in vehicles containing about 30% to about 100% acetone so that the benzoyl peroxide is solubilized. Cloth pledgettes made of cotton, wool, nylon, rayon or other synthetic fabrics are then impregnated with such compositions and the resulting individual benzoyl peroxide pledgettes preferably are packaged in individual pouches, such as foil or plastic. Individual benzoyl peroxide pouches are then opened, the pledgette removed, and the pledgette rubbed across the surface of the face or other acne bearing area which the patient intends to treat for acne. Following use in this fashion, individual pledgettes are then discarded.

The instant invention thus relates to an article for use in the treatment of acne vulgaris, the article comprising a fiber pledgette impregnated with a composition comprising benzoyl peroxide and an amount of acetone sufficient to solubilize the benzoyl peroxide. Preferably, the pledgettes are packaged in individual pouches. The instant invention also comprises the method of manufacturing an article for use in the treatment of acne vulgaris comprising impregnating fiber pledgettes with a composition comprising benzoyl peroxide and an amount of acetone sufficient to solubilize the benzoyl peroxide, preferably packaging the pledgettes in individual pouches. The pouches can comprise known flexible, impermeable, sealable non-reactive materials such as aluminum foil, plastic film, or combinations of such materials.

The composition used to impregnate the cloth pledgette comprises benzoyl peroxide in the range of about 2–10%, and most preferably about 4.0–10%. Purified water is optionally present in an amount ranging from 0% to about 65%. Other optional ingredients include polyethylene glycol 400, which can be present in the range of about 0–15%, and glycerin which can be present in the range of about 0–20%. The balance of the composition is acetone. In a preferred embodiment the composition will comprise at least about 30% acetone.

The composition is prepared by blending the selected ingredients at ambient temperature until solubilization of the benzoyl peroxide is complete. Pledgettes of a desired fabric are then impregnated with the composition. Preferably, the pledgettes are packaged in individual pouches.

The following examples illustrate the present invention.

EXAMPLE 1

A composition comprising benzoyl peroxide 4.5%, acetone 69.0%, purified water 16.5%, and polyethylene glycol 400 10.0% was prepared and used to impregnate cotton pledgettes. Twenty-three acne patients ages 18–25 years applied the resulting product to their cheeks for five days with excellent results.

EXAMPLE 2

A composition comprising benzoyl peroxide 5.5%, acetone 67.0%, purified water 15.0%, and polyethylene glycol 400 12.5% was prepared and used to impregnate rayon pledgettes. Twenty-three acne patients ages 18–25 years applied the resulting product to the cheeks for five days with excellent results.

EXAMPLE 3

A composition comprising benzoyl peroxide 2.5%, acetone 35.0%, purified water 57.5%, and glycerin 5.0% was prepared and used to impregnate cotton pledgettes.

EXAMPLE 4

A composition comprising benzoyl peroxide 10.0%, acetone 88.2%, and purified water 1.8% was prepared and used to impregnate cotton pledgettes.

EXAMPLE 5

A composition comprising benzoyl peroxide 5.5%, acetone 73.5%, purified water 15.9%, and glycerin 5.0%. The resulting formulation was used to impregnate cotton pledgettes.

While the foregoing is a description of the preferred embodiments of the instant invention it will be readily apparent to those skilled in the art that various modifications may be made therein without departing from the true scope and spirit of the invention as set forth in the appended claims.

What is claimed is:

1. An article comprising a fiber pledgette impregnated with a liquid composition comprising about 2–10% benzoyl peroxide, at least about 30% acetone, water, and either polyethylene glycol or glycerine, the article being suitable for use in the application of benzoyl peroxide to the skin of a person afflicted with acne vulgaris for the treatment of acne vulgaris.

2. The article of claim 1 wherein said benzoyl peroxide is present in said solution in the amount of about 4.0–10%.

3. The article of claim 1 wherein said polyethylene glycol comprises polyethylene glycol 400.

4. The article of claim 3 wherein said polyethylene glycol 400 is present in said composition in an amount up to about 15%.

5. The article of claim 1 wherein said glycerin is present in said composition in an amount up to about 20%.

6. The article of claim 1 wherein said pledgette is made from a cloth containing fibers selected from the group consisting of cotton, wool, nylon, and rayon.

7. The article of claim 1 wherein said impregnated pledgette is packaged in an individual pouch.

8. The article of claim 7 wherein said pouch comprises foil.

9. The article of claim 7 wherein said pouch comprises plastic film.

10. A method of manufacturing an article for use in the treatment of acne vulgaris, the method comprising the steps of
    (a) providing a liquid composition comprising about 2–10% benzoyl peroxide, about at least 30% acetone, water, and either polyethylene glcol or glycerine, and
    (b) impregnating a fiber pledgette with said liquid composition, such that said impregnated fiber pledgette is suitable for use in the application of benzoyl peroxide to the skin of a person afflicted with acne vulgaris for the treatment of acne vulgaris.

11. The method of claim 10 wherein said composition is prepared with benzoyl peroxide present in the amount of about 4.0–10%.

12. The method of claim 10 wherein said polyethylene glycol comprises polyethylene glycol 400.

13. The method of claim 12 wherein said composition is prepared with polyethylene glycol 400 in an amount of up to about 15%.

14. The method of claim 10 wherein said composition is prepared with glycerin.

15. The method of claim 14 wherein said composition is prepared with glycerin in an amount of up to about 20%.

16. The method of claim 10 wherein said pledgette is made from a cloth containing fibers selected from the group consisting of cotton, wool, nylon, and rayon.

17. The method of claim 10 including the further step of packaging said pledgette in an individual pouch.

18. The method of claim 17 wherein said pouch comprises foil.

19. The method of claim 17 wherein said pouch comprises plastic film.

20. A method of treating acne vulgaris, the method comprising the steps of
    (a) providing a fiber pledgette impregnated with a liquid composition comprising about 2–10% benzoyl peroxide, at least about 30% acetone, water, and either polyethylene glycol or glycerine, and
    (b) using said impregnated fiber pledgette to apply benzoyl peroxide to the skin of a person afflicted with acne vulgaris.

21. The method of claim 20 wherein said benzoyl peroxide is present in said solution in the amount of about 4.0–10%.

22. The method of claim 20 wherein said polyethylene glycol comprises polyethylene glycol 400.

23. The method of claim 22 wherein said polyethylene glycol 400 is present in said composition in an amount up to about 15%.

24. The method of claim 20 wherein said glycerin is present in said composition in an amount up to about 20%.

25. The method of claim 20 wherein said pledgette is made from a cloth containing fibers selected from the group consisting of cotton, wool, nylon, and rayon.

26. The method of claim 20 wherein said impregnated pledgette is packaged in an individual pouch.

27. The method of claim 26 wherein said pouch comprises foil.

28. The method of claim 26 wherein said pouch comprises plastic film.

* * * * *